United States Patent
Jeon et al.

(10) Patent No.: US 10,750,762 B2
(45) Date of Patent: Aug. 25, 2020

(54) BIO-BASED N-ACETYL-L-METHIONINE AND USE THEREOF

(71) Applicant: CJ Cheiljedang Corporation, Seoul (KR)

(72) Inventors: Jin Woo Jeon, Gyeonggi-do (KR); Jun Ok Moon, Gyeonggi-do (KR); Jin Seung Park, Gyeonggi-do (KR); Su Jin Choi, Daegu (KR); Kuk Ki Hong, Gyeonggi-do (KR); Jeong Hyun Kim, Jeollanam-do (KR); Hye Min Park, Gyeongsangnam-do (KR); So Yeon Hong, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 15/766,325

(22) PCT Filed: Oct. 14, 2016

(86) PCT No.: PCT/KR2016/011577
§ 371 (c)(1),
(2) Date: Apr. 5, 2018

(87) PCT Pub. No.: WO2017/065567
PCT Pub. Date: Apr. 20, 2017

(65) Prior Publication Data
US 2018/0317522 A1    Nov. 8, 2018

(30) Foreign Application Priority Data

Oct. 14, 2015  (KR) .................. 10-2015-0143428
Jul. 20, 2016  (KR) .................. 10-2016-0092089

(51) Int. Cl.
*A23K 20/142*  (2016.01)
*C12P 13/12*  (2006.01)
*A23K 50/10*  (2016.01)
*A23K 10/12*  (2016.01)
*A23K 10/14*  (2016.01)
*A23K 10/18*  (2016.01)
*A61K 31/198*  (2006.01)

(52) U.S. Cl.
CPC ............ *A23K 20/142* (2016.05); *A23K 10/12* (2016.05); *A23K 10/14* (2016.05); *A23K 10/18* (2016.05); *A23K 50/10* (2016.05); *A61K 31/198* (2013.01); *C12P 13/12* (2013.01)

(58) Field of Classification Search
None
See application file for complete search history.

(56) References Cited

U.S. PATENT DOCUMENTS

| | | | |
|---|---|---|---|
| 3,878,305 A | 4/1975 | Damico et al. | |
| 4,011,263 A | 3/1977 | Wagner et al. | |
| 4,994,457 A | 2/1991 | Crawford et al. | |
| 8,143,031 B2 | 3/2012 | Figge et al. | |
| 2010/0047880 A1 | 2/2010 | Figge et al. | |
| 2010/0115661 A1 | 5/2010 | Duesing et al. | |
| 2015/0045434 A1 | 2/2015 | Fiey | |
| 2015/0211034 A1 | 7/2015 | Kim et al. | |

FOREIGN PATENT DOCUMENTS

| | | | |
|---|---|---|---|
| CA | 1067334 A | 12/1979 | |
| CN | 102131923 A | 7/2011 | |
| JP | S5871892 A | 4/1983 | |
| JP | 2012-500623 A | 1/2012 | |
| KR | 10-2002-0047880 A | 6/2002 | |
| KR | 10-0905381 B1 | 1/2008 | |
| KR | 10-2011-0042383 A | 4/2011 | |
| WO | WO 2012/090021 A1 | 7/2012 | |

OTHER PUBLICATIONS

Ferla et al., Microbiology (2014), 160, pp. 1571-1584.*
Office Action in Korean Patent Application No. 10-2016-0092089, dated May 31, 2017.
Office Action in Taiwanese Patent Application No. 105133230, dated Feb. 8, 2018.
Ouoba et al., "Degradation of proteins during the fermentation of African lucust bean (*Parkia biglobosa*) by strains of Bacillus subtilis and Bacillus pumilus for production of Soumbala," Journal of Applied Microbiology, vol. 94(3), pp. 396-402, 2003.
Office Action issued in New Zealand Patent Application No. 741423, dated Sep. 18, 2019.
H.E. Amos et al: "Methionine, DL-Homocysteine Thiolactone and N-Acetyl-DL-Methionine for Ruminants", Journal of Animal Science, vol. 39, No. 3, Sep. 1, 1974 (Sep. 1, 1974), pp. 612-617, XP055558606.
Partial Supplementary European Search Report issued in European Patent Application No. 16855784.1, dated May 16, 2019.
Office Action issued in New Zealand Patent Application No. 741423, dated Nov. 12, 2018.
Office Action issued in Japanese Patent Application No. 2018-519350, dated Apr. 2, 2019.
Extended Search Report issue in European Patent Application No. 16855784.1, dated Aug. 5, 2019.

* cited by examiner

*Primary Examiner* — Brian J Davis
(74) *Attorney, Agent, or Firm* — Knobbe Martens Olson & Bear LLP (57) ABSTRACT

A bio-based N-acetyl-L-methionine and a preparation method thereof, a feed additive containing the N-acetyl-L-methionine, a feed composition containing the feed additive, and a method for raising animals which includes feeding a feed additive containing the N-acetyl-L-methionine or a feed composition containing the feed additive to animals.

18 Claims, 1 Drawing Sheet

BIO-BASED N-ACETYL-L-METHIONINE AND USE THEREOF

CROSS-REFERENCE TO RELATED APPLICATIONS

This application is the U.S. National Phase under 35 U.S.C. § 371 of International Application PCT/KR2016/011577, filed Oct. 14, 2016, which was published in English as WO 2017/065567 on Apr. 20, 2017, which claims priority to Korean Patent Application No. 10-2015-0143428, filed Oct. 14, 2015, and Korean Patent Application No. 10-2016-0092089, filed Jul. 20, 2016, the entire contents of which are incorporated herein by reference.

TECHNICAL FIELD

The present disclosure relates to bio-based N-acetyl-L-methionine and a preparation method thereof. Additionally, the present disclosure relates to a feed additive and a feed composition including bio-based N-acetyl-L-methionine.

BACKGROUND ART

In order to maintain life, form new tissues, and continue an activity for producing milk, meats, eggs, etc., animals must be continuously supplied with sufficient nutrients provided in vitro. Therefore, there have been many attempts to increase characteristics, such as rate of gain, and meat texture, by directly feeding animals amino acids, essential nutrient elements, in addition to an animal feed. However, 60% to 70% of most amino acids digested by a ruminant are autonomously consumed via the digestive process of microorganisms in a ruminant stomach (more specifically, rumen), while some undigested amino acids are merely digested or absorbed in the small intestine. Accordingly, although amino acids are added in feeds for ruminants, an effect such as that in hog-raising and poultry-raising cannot be obtained, and therefore, it is necessary to develop rumen-protected amino acids which bypass the rumen while being capable of being digested by ruminants.

That is, in a case in which amino acids must be added in the feeds for ruminants, the amino acids must be absorbed and safely reach the small intestine while avoiding degradation by microorganisms in the rumen. Therefore, the need for an effect of protecting from the rumen or improved novel technology of bypassing the rumen and materials thereof has recently been highlighted.

On the other hand, even though N-acetyl-L-methionine is a material that is known to be used in food additives or animal feeds, the demand for N-acetyl-L-methionine is limited due to its high preparation costs. Additionally, a conventional preparation method thereof uses materials derived from petroleum, which accordingly causes depletion of limited resources and environmental problems (U.S. Pat. No. 7,960,575).

A specific example for the conventional preparation method of N-acetyl-L-methionine refers to a method for producing N-acetyl-L-methionine by acetylation of L-methionine, which is separated from D/L-methionine had prepared by chemical synthesis from petroleum. However, it has some disadvantages in that it takes high costs to separate only L-methionine from D/L-methionine mixtures.

Additionally, the direct fermentation method, in which the L-form can be obtained by over-expressing an acetylating enzyme in methionine-producing strains, has been discovered (U.S. Pat. No. 8,143,031). However, such method has indirectly confirmed that YncA may use acetyl coenzyme A (acetyl-CoA) by DTNB analysis, but has not been confirmed whether N-acetyl-L-methionine is substantially prepared as an enzyme reaction product or a product producing transformants of the gene. Further, the method has a difficulty in commercialization due to its high costs followed by the lowered yield.

DISCLOSURE OF INVENTION

Technical Problem

The present inventors have carried out extensive research in order to develop a method for producing N-acetyl-L-methionine, in which the method is environmentally friendly due to less production of carbon dioxide in the entire process, while having high efficiency and economic feasibility. As a result, the inventors have produced bio-based L-methionine with high yield and economically developed the method for production thereof without concerns of environmental contamination, by acetylating the bio-based L-methionine. Thereby, the present disclosure was completed.

Solution to Problem

An object of the present disclosure is to provide a method for producing bio-based N-acetyl-L-methionine, including: (a) (i) producing L-methionine precursor by microorganism fermentation; (ii) producing L-methionine from the L-methionine precursor by enzymatic conversion; and (b) acetylating the L-methionine.

Another object of the present disclosure is to provide a method for producing bio-based N-acetyl-L-methionine, including: (a) producing L-methionine by microorganism fermentation; and (b) acetylating the L-methionine.

Yet another object of the present disclosure is to provide a method for producing bio-based N-acetyl-L-methionine, including directly producing the bio-based N-acetyl-L-methionine by fermentation of a microorganism producing N-acetyl-L-methionine having an acetylating enzyme activity.

A further object of the present disclosure is to provide bio-based N-acetyl-L-methionine including carbon derived from bioresources.

A further object of the present disclosure is to provide a population of bio-based N-acetyl-L-methionine, wherein 50% to 100% of the carbon constituting the population is carbon derived from bioresources.

A further object of the present disclosure is to provide a feed additive including the bio-based N-acetyl-L-methionine or a salt thereof.

A further object of the present disclosure is to provide a feed composition including the bio-based N-acetyl-L-methionine or a salt thereof.

A further object of the present disclosure is to provide a method for improving milk production, milk fat, or milk proteins, or a weight-gain effect of an animal, including feeding a feed additive or a feed composition.

Advantageous Effects of Invention

A method for producing the bio-based N-acetyl-L-methionine of the present disclosure is performed using bioresources, and thus not only causes less environmental contamination but also economically produces the N-acetyl-L-methionine with high yield. Accordingly, the method can be very effectively used in the industry. In particular, N-acetyl-L-methionine produced by such method exhibits a remarkable effect as a feed additive, as the N-acetyl-L-methionine is capable of bypassing the rumen.

BEST MODE FOR CARRYING OUT THE INVENTION

In order to achieve the above objects, an aspect of the present disclosure is a method for producing bio-based N-acetyl-L-methionine, including (a) (i) producing an L-methionine precursor by microorganism fermentation; and (ii) producing L-methionine from the L-methionine precursor by enzymatic conversion; and (b) acetylating the L-methionine.

Another aspect of the present disclosure is a method for producing bio-based N-acetyl-L-methionine, including (a) producing L-methionine by microorganism fermentation; and (b) acetylating the L-methionine.

As used herein, the term "bio-based" refers to a material derived from bioresources. The term "bioresources" includes all materials obtainable from various algae and plant resources, produced by the photosynthesis, i.e., a tree, a grass, a branch of crops, a leaf, a root, a fruit, etc., in particular, refers to environmentally friendly resources other than petroleum resources.

The method for producing N-acetyl-L-methionine of the present disclosure is a method for producing an L-methionine precursor with high efficiency by fermenting a bio-carbon source, instead of using a petroleum-derived material, and a method for producing N-acetyl-L-methionine (NALM) therefrom. Therefore, the method is industrially very effective as an environmentally friendly and economical way.

Hereinafter, the method for producing N-acetyl-L-methionine of the present disclosure will be described in more detail.

Step (a) includes (i) producing an L-methionine precursor by microorganism fermentation; and (ii) producing L-methionine from the L-methionine precursor by enzymatic conversion.

The L-methionine precursor refers to a compound that can be converted into L-methionine among materials produced by fermenting a bio-carbon source, and may refer to O-acetyl-L-homoserine or O-succinyl-L-homoserine, but is not limited thereto.

A microorganism used for the above fermentation refers to a strain capable of producing an L-methionine precursor. Additionally, as used herein, the term "strain capable of producing an L-methionine precursor" refers to a prokaryotic or eukaryotic microbial strain producing an L-methionine precursor in an organism, and further, refers to a strain capable of accumulating the L-methionine precursor therein. The strain capable of producing the L-methionine precursor may refer to producing strain of O-succinyl-L-homoserine or O-succinyl-L-homoserine.

For example, the strain may include a microbial strain belonging to *Escherichia* sp., *Erwinia* sp., *Serratia* sp., *Providencia* sp., *Corynebacteria* sp., *Pseudomonas* sp., *Leptospira* sp., *Salmonellar* sp., *Brevibacteria* sp., *Hypomononas* sp., *Chromobacterium* sp., *Norcardia* sp., fungi, or yeasts; specifically, the strain may be a microbial strain belonging to *Escherichia* sp., *Corynebacteria* sp., *Leptospira* sp., and yeasts; more specifically, it may be a microbial strain belonging to *Escherichia* sp.; and most specifically, the strain may be *Escherichia coli*, but is not limited thereto.

Additionally, the above strain may include the strain disclosed in U.S. Pat. Nos. 8,609,396 and 7,851,180.

As used herein, the term "fermentation" refers to degradation of organic materials by microorganisms which cause simple production of organic compounds. The fermentation may occur under anaerobic conditions or in the presence of oxygen. In particular, the fermentation may be carried out by culturing the strain producing an L-methionine precursor.

A process of culturing strain producing the prepared L-methionine precursor may be carried out in accordance with the sufficient medium and culture condition known in the art. Such culture process may be easily used with adjustments in accordance with the strains selected by one of ordinary skill in the art. Examples of the culture method may include batch, continuous, and fed-batch cultures, but is not limited thereto.

The medium used in the culture should appropriately meet the required conditions of a specific strain. The culture medium may include various carbon sources, further, may include other nitrogen sources and components of a microelement. The carbon source is characterized in that it particularly includes bio-based materials. Specifically, the bio-carbon source may include carbohydrates such as sugar, glucose, lactose, sucrose, fructose, maltose, starch, and cellulose; fats such as soybean oil, sunflower oil, castor oil, beaver oil, and coconut oil; fatty acids such as palmitic acid, stearic acid, and linoleic acid; alcohols such as glycerol and ethanol; and organic acids such as acetic acid, but are not limited thereto. These carbon sources may be used alone or in combination. Examples of the nitrogen sources may include organic nitrogen sources such as peptone, yeast extract, gravy, malt extract, corn steep liquor (CSL), and bean flour; and inorganic nitrogen sources such as urea, ammonium sulfate, ammonium chloride, ammonium phosphate, ammonium chloride, ammonium phosphate, ammonium carbonate, and ammonium nitrate. These nitrogen sources may be used alone or in combination. The culture media may further include, as a phosphorous source, potassium dihydrogen phosphate, potassium hydrogen phosphate, and corresponding sodium-containing salts. The culture medium may include metals such as magnesium sulfate or iron sulfate. Additionally, amino acids, vitamins, and appropriate precursors may be included. The culture medium or precursors may be added to the culture in the form of a batch culture or a continuous culture.

Additionally, the pH of the culture may be adjusted by adding a compound such as ammonium hydroxide, potassium hydroxide, ammonia, phosphoric acid, and sulfuric acid during culture in an appropriate manner. Additionally, bubble formation may be prevented during the culture using an antifoaming agent such as fatty acid polyglycol ester. Additionally, in order to maintain aerobic conditions in the culture medium, an oxygen gas or a gas (e.g., air) containing an oxygen gas may be added to the culture. In general, the culture temperature may be 20° C. to 45° C., and specifically 25° C. to 45° C. The culture may be continued until the production of the L-methionine precursors reaches the intended level, and the culture time may be 10 hours to 160 hours, but is not limited thereto.

The enzymatic conversion process refers to a process converting L-methionine precursor into L-methionine by using an enzyme. Specifically, the enzyme used during the enzymatic conversion process may be at least one enzyme selected from the group consisting of cystathionine-γ-synthase, O-acetyl homoserine sulfhydrylase, and O-succinyl homoserine sulfhydrylase, but is not limited thereto. Specifically, the enzymatic conversion refers to a process reacting with the enzyme upon the addition of methyl-mercaptan to the L-methionine precursor or the fermentation medium containing the same, but is not limited thereto.

Additionally, above step (a) may refer to a step directly producing L-methionine by microorganism fermentation. In such a case, the microorganism used in the fermentation refers to a strain capable of producing L-methionine. Further, as used herein, the term "strain capable of producing L-methionine" refers to a prokaryotic or eukaryotic microbial strain producing L-methionine in an organism, and thus refers to a strain capable of accumulating the L-methionine in the strain.

For example, the strain may include a microbial strain belonging to *Escherichia* sp., *Erwinia* sp., *Serratia* sp., *Providencia* sp., *Corynebacteria* sp., *Pseudomonas* sp., *Leptospira* sp., *Salmonellar* sp., *Brevibacteria* sp., *Hypomononas* sp., *Chromobacterium* sp., *Norcardia* sp., fungi, or yeasts; specifically, a microorganism strain belong to *Escherichia* sp., *Corynebacteria* sp., *Leptospira* sp., and yeasts; more specifically, a microorganism strain belonging to *Escherichia* sp.; and most specifically, the strain may be *Escherichia coli*, but is not limited thereto. Additionally, the strain above may include the strain disclosed in Korean Patent No. 10-1140906.

Step (b) refers to a step of acetylating the L-methionine.

The method of acetylating the L-methionine may be carried out by a chemical synthesis method, a production method by microorganisms, or an acetylating enzyme, but is not limited thereto. Additionally, one of ordinary skill in the art could appropriately use and select the method from any methods capable of acetylating L-methionine.

The chemical synthesis method refers to a process of injecting a compound capable of acetylating an amine group of L-methionine to react at room temperature or high temperature. The base material, which can be used in the acetylation reaction of L-methionine, may be acetic anhydride, and further, the acetic acid accompanying transition metal-based catalyst may be used. Additionally, for the moderate reaction condition in which an aprotic solvent is applied, acetyl halide can be used as the acetylating compound. In the present disclosure, the high temperature may refer to 70° C. to 100° C., and specifically, 80° C. to 90° C., but is not limited thereto.

Additionally, the acetylation may be carried out by adding purified acetylating enzymes or supernatant of the disrupted microorganism expressing the acetylating enzyme into a mixture containing L-methionine and acetyl-CoA. The acetylating enzyme includes acyltransferase capable of converting L-methionine into N-acetyl-L-methionine. For example, the acetylating enzyme may be L-amino acid N-acyltransferase MnaT (YncA), N-acetylglutamate synthase (ArgA), putative acetyltransferase (YjdJ), putative acetyltransferase (YfaP), putative acetyltransferase (YedL), or putative acetyltransferase (YjhQ), but is not limited thereto.

The acetylating enzyme may be obtained from *Escherichia coli, Corynebacterium*, or yeasts, transformed to express the above mentioned enzyme. That is, *Escherichia coli*, yeast, or *Corynebacterium* is transformed using the gene which codes for each of acetylating enzymes. Thereafter, the purified acetylating enzyme can be used after the transformant thereof is cultured, or used by collecting a supernatant upon disruption of the transformed strain. Additionally, the acetylation may be induced by supplying L-methionine, after permeability of a cell wall in the strain is increased via a pretreatment process using xylene, without disrupting the transformed strain Furthermore, the acetylation may be carried out using an acetylating enzyme reaction within a strain, while the strain is cultured by microorganism fermentation at the corresponding time. The direct fermentation by microorganisms may use a wild-type strain which inherently includes the enzyme capable of acetylating L-methionine; use a mutant having the feature in which the acetylating enzyme activity is enhanced through artificial mutation; or use the transformed strain which is improved due to over-expression of an enzyme capable of inducing the acetylation of L-methionine. That is, any microorganisms which produce N-acetyl-L-methionine having the activity of the acetylating enzyme can be used without limitation. Additionally, the production of N-acetyl-L-methionine is possible through the acetylation reaction by not only using L-methionine biosynthesized within microorganisms, but also using L-methionine supplied from an outside source during the fermentation.

When an acetylating enzyme or a microorganism producing the same is used during the acetylating process of L-methionine, it may include a step of supplying acetyl-CoA. That is, the step may be carried out by directly supplying the acetyl-CoA, or by adding glucose or acetic acid so that sufficient amounts of the acetyl-CoA can be supplied to microorganisms.

The present disclosure relates to the preparation of an L-methionine precursor by fermentation, and then prepares L-methionine in high yields through an enzymatic conversion process, or relates to the preparation of N-acetyl-L-methionine with various acetylation methods, upon direct preparation of the L-methionine in high yields through the fermentation. Accordingly, the present disclosure suggests a novel paradigm which is completely different from conventional methods of preparing petroleum-based N-acetyl-L-methionine.

Additionally, with the present disclosure, the production ability of N-acetyl-L-methionine can be significantly increased by direct fermentation using a wild type microorganism having an inherent capability of N-acetyl-L-methionine production, an artificial mutant thereof or transformed strains in which the production ability of N-acetyl-L-methionine is improved by the introduction of acetylating enzymes, or a conversion reaction. Further, based on the same, efficiency of a biological production method of N-acetyl-L-methionine exhibiting the low production ability also can be significantly improved.

At least 50% of carbon constituting the N-acetyl-L-methionine may be carbon derived from bioresources. For example, at least 50% of the carbon constituting N-acetyl-L-methionine produced from the method for producing the N-acetyl-L-methionine may be derived from O-acetyl-L-homoserine, which refers to the L-methionine precursor obtained by fermenting bio-carbon sources, or O-succinyl-L-homoserine.

The N-acetyl-L-methionine contains at least 50% of bio-derived carbon because base materials constituting an element are derived from bio-derived carbon. The molecular weight of N-acetyl-L-methionine is 191.25 g/mol, and the N-acetyl-L-methionine is constituted of L-homoserine (119.12 g/mol), methyl-mercaptan (48.11 g/mol), and acetic acid (59.04 g/mol). During the conjugation, a hydroxyl group in L-homoserine and hydrogen in methyl-mercaptan are separated, and a hydroxyl group in the acetic acid and hydrogen in the L-homoserine are separated in order to prepare the final N-acetyl-L-methionine. L-homoserine is obtained through fermentation using bioresources, and possesses at least 50% of the entire molecular weight in N-acetyl-L-methionine (L-homoserine 119.12 g/mol-H$_2$O 18.01 g/mol=101.11 g/mol, this numerical value indicates at least 50% of the molecular weight of the N-acetyl-L-methionine). Additionally, in a case when an acetylating enzyme is used, a content of the bio-derived carbon in N-acetyl-L-methionine would be increased because acetic acid is also derived from bioresources (L-homoserine without H$_2$O 101.11 g/mol+acetic acid without a hydroxyl group 42.04 g/mol=143.15 g/mol, it possesses at least 75% of the N-acetyl-L-methionine).

On the other hand, it is possible to determine whether the material is bio-derived or petroleum-derived by measuring its radiocarbon. That is, there are three isotopes ($^{12}$C, $^{13}$C, $^{14}$C) present in carbon, but most of $^{14}$C (radiocarbon) does not exist in petroleum material carbon sources. Therefore, based on the scientific fact that $^{14}$C exists only in bio-derived carbon, the content analysis of $^{14}$C is carried out so as to determine whether or not the material is bio-derived.

Another aspect of the present disclosure refers to bio-based N-acetyl-L-methionine including bio-derived carbon.

50% to 100% of carbon constituting the bio-based N-acetyl-L-methionine may be carbon derived from bioresources.

Still another aspect of the present disclosure refers to a population of bio-based N-acetyl-L-methionine, wherein 50% to 100% of carbon constituting N-acetyl-L-methionine is carbon derived from bioresources.

The bio-based N-acetyl-L-methionine may be produced by the production method above.

Bioresources, bio-based N-acetyl-L-methionine, and the production method thereof are as described above.

In another aspect, the present disclosure provides bio-based N-acetyl-L-methionine or a feed additive including a salt thereof.

In still another aspect, the present disclosure provides bio-based N-acetyl-L-methionine or a feed composition including a salt thereof.

The N-acetyl-L-methionine is as described above.

As used herein, the term "feed additive" refers to a material added to a feed composition. The feed additive may increase productivity of a subject animal or improve health, but is not limited thereto.

The feed additive may be used for ruminants, but is not limited thereto.

The present disclosure uses the N-acetyl-L-methionine or a feed additive including a salt thereof, wherein the feed additive may additionally include nutrients, such as nucleotides, amino acids, calcium, phosphate, organic acids, etc., for improving productivity of a subject animal or health, in addition to the N-acetyl-L-methionine or a salt thereof, but is not limited thereto.

As used herein, the term "feed composition" refers to a feed given to animals. The feed composition refers to a material providing organic nutrients or mineral nutrients which are necessary to maintain life of animals or to produce meat, milk, etc. The feed composition may include a feed additive, and the feed additive of the present disclosure may correspond to a supplementary feed in accordance with Control of Live and Fish Feed Act.

Types of the feed above are not specifically limited, and any conventional feeds that used in the art to which the present disclosure pertains can be used. Non-limiting examples of the feed may include vegetable feeds, such as grains, roots/fruits, food processing byproduct, algae, fibers, pharmaceutical byproducts, oils and fats, starches, gourds, and grain byproducts; and animal feeds, such as proteins, inorganic materials, oils and fats, minerals, single-cell proteins, animal plankton, and food residue. These may be used alone or in a combination of two or more.

Animals that can be applied with the feed composition of the present disclosure are not specifically limited, but it is possible to apply to any kinds. For example, the feed composition can be applied to animals, such as cattle, sheep, giraffe, camels, deer, goat, etc., without limitation, and specifically applicable to a ruminant having the rumen. A domestic cow can be a representative example thereof, but is not limited thereto.

According to one embodiment of the present disclosure, N-acetyl-L-methionine or a salt thereof may be used as a rumen-protected peptide derivative due to its low degradation by microorganisms in the rumen. Therefore, the N-acetyl-L-methionine or the salt thereof may be effectively used as a feed additive for ruminants, but is not limited thereto.

As used herein, the term "ruminant stomach" refers to a special digestive tract that can be found in some mammals, and is divided into four compartments consisting of rumen, reticulum, omasum, and abomasums for rumination. Rumination refers to the process by which the mammal regurgitates previously consumed feed and masticates it for a second time, and the stomach capable for this rumination is called a ruminant stomach. Because microorganisms live in the rumen in a symbiotic manner, the rumen has a capability of degrading the cellulose of a plant, which animals do not generally digest, and such degraded cellulose can be used as energies.

As used herein the term "ruminant" refers to an animal having the ruminant stomach described above, and includes members in an animal of camelidae, chevrotain family, cervidae, giraffidae, and bovidae. However, camels and chevrotains are known to have three compartments of the ruminant stomach because omasum and abomasum are not fully differentiated.

The feed additive may be added to a feed composition to include the N-acetyl-L-methionine or a salt thereof, in an amount of 0.01 wt. % to 90 wt. %, relative to the total weight of the feeds, but is not limited thereto.

Additionally, the feed additive according to the present disclosure may be used separately; may be used in combination with a conventional feed additive; and may be used sequentially or simultaneously with a conventional feed additive. Further, the feed additive may be administered with a single dose or a multiple dose. It is significant to entirely consider the above factors to administer an amount capable of achieving the maximum effect with the minimum amount, without side effects, and further, it can be easily determined by one of ordinary skill in the art.

Another aspect of the present disclosure refers to a granular formulation including the bio-based N-acetyl-L-methionine or microorganisms producing the same.

Bio-based N-acetyl-L-methionine and microorganisms producing the same are as described above.

The granular formulation may be prepared by directly forming granules from fermentation culture medium of a microorganism having N-acetyl-L-methionine, or may be prepared by including the microorganism. Additionally, the granular formulation may be prepared by including both the fermentation culture medium and microorganism. One of ordinary skill in the art may carry out the formation process of granules with an appropriate selection, but is not limited thereto.

Products may be provided through optimizing the operation method of a granulation dryer and by the recycling process of a non-standard product, wherein the range in the particle size of final products less than or equal to 500 μm is 0% to 5%; the particle size greater than 500 μm but less than or equal to 1000 μm is 20% to 30%; the particle size greater than 1000 μm but less than or equal to 1300 μm is 60% to 70%; and the particle size greater than 1300 μm is 5%, but is are not limited thereto.

In an exemplary embodiment, the present disclosure provides the preparation method of a granular formulation including: concentrating the fermentation culture medium of N-acetyl-L-methionine to a total solid content of 40 wt. % to 50 wt. %; forming a mixed concentrate by adding and mixing at least one selected from the group consisting of a diluting agent and free N-acetyl-L-methionine into the concentrated culture medium; and injecting particle seeds, in which the size thereof is 200 μm to 500 μm, into a granulator, coating the particle seeds by spraying the mixed concentrate from the lower part of the granulator, and forming onion-shaped granules by increasing the size of the particle seeds, thereby the range in the particle size less than or equal to 500 μm is 0% to 5%, greater than 500 μm but less than or equal to 1000 μm is 20% to 30%, greater than 1000 μm but less than or equal to 1300 μm is 60% to 70%, and greater than 1300 μm is 5%.

For example, the granular formulation according to the present disclosure may contain fermentation culture medium of N-acetyl-L-methionine as a main ingredient, by the granulation having the compositions and features below.

N-acetyl-L-methionine content of more than 50 wt. %;

Particle size of less or equal to 500 μm is 0% to 5%, greater than 500 μm but less than or equal to 1000 μm is 20% to 30%, greater than 1000 μm but less than or equal to 1300 μm is 60% to 70%, and greater than 1300 μm is 5% (based on the weight);

Apparent density 670±50 kg/m$^3$;

Protein 10 wt. % to 15 wt. %;

Total sugar less than or equal to 1 wt. %;

Mineral less than or equal to 3 wt. %;

Water less than or equal to 3 wt. %.

The final content of granular products can be adjusted to the desired content by con-trolling the amount of an added free N-acetyl-L-methionine or an excipient in the process of forming a mixed concentrate. The granulation may be carried out by spraying the mixed concentrate with a nozzle on the lower part of the granulator, while applying a hot air to form a fluidized bed.

The size of particles obtained in step of the granulation may be accomplished by adjusting the flow rates of the mixed concentrate, nozzle pressures, or air volumes of a hot air.

The excipient may be at least one selected from the group consisting of starch, carrageenan, and sugar, but is not limited thereto.

The microorganisms producing N-acetyl-L-methionine used in the production of the granular formulation may be microorganisms that is classified by GRAS (Generally Recognized as Safe). Specifically, the microorganisms may be microorganisms belonging to *Corynebacterium* sp. which has high protein content, or microorganisms belong to *Yarrowia* sp. which has high fat content, but are not limited thereto.

The fermentation condition of microorganisms are not particularly limited, but it may be culturing microorganisms with a condition in which the large amount of N-acetyl-L-methionine is accumulated during the fermentation while less cell mass is accumulated. Additionally, sugars in fermentation culture medium prevent the drying of the fermentation culture medium, and increase the hygroscopicity of the products that will be obtained, and thus it may be culturing the microorganisms in a condition reducing the amount thereof. However, in the present disclosure, the content of N-acetyl-L-methionine can be adjusted by the mixing process, and the surface of the product is compacted due to the special feature of the granulation process. Therefore, a fermentation condition should not necessarily be limited to the condition described above.

In the present disclosure, the hygroscopic reduction effect is present without an addition of an anti-hygroscopic agent. However, if necessary, silica, a polymer, etc., specifically liquid paraffin may be added as the anti-hygroscopic agent.

Another aspect of the present disclosure refers to a method of improving an effect of gaining of body weight or increasing animals' milk production, milk fats, or milk proteins, in which includes feeding a feed additive containing the bio-based N-acetyl-L-methionine or the salt thereof, or feeding a feed composition. The feed additive or the feed composition is as described above.

The method may particularly include steps of: (a) mixing the feed additive or the feed composition in an animal feed; and (b) feeding the animal feed to animals.

Step (a) according to the present disclosure is a step for mixing the animal feed composition including the N-acetyl-L-methionine or a salt thereof of the present disclosure with regular feeds for a livestock, and thus may mix the same within the range of 0.01 wt. %. to 90 wt. %, or specifically 0.1 wt. %. to 10 wt. %.

Step (b) according to the present disclosure is a step of feeding the feed prepared in step (a) to animals, and thus a livestock that can be fed is not specifically limited as described above, and it may particularly be a ruminant.

When the feed additive or the feed composition according to the present disclosure is fed to animals, a remarkable effect, such as an effect of enhancing or increasing animals' milk production, milk fats, or milk proteins, or gaining body weight may be expected.

MODE FOR THE INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Production of Bio-Based L-Methionine

Example 1-1. Fermentation of a Strain Producing L-Methionine Precursor

The culture of a fermenter (5 L) was carried out in order to massively produce L-methionine precursors (O-acetyl homoserine) using *Escherichia coli* CJM-BTJA/pCJ-MetX-lme-CL (Korean Patent No. 10-0905381), which refers to strains producing O-acetyl homoserine, as the strains producing the L-methionine precursor. These strains were inoculated on LB plate medium containing antibiotics, and then cultured overnight at 31° C. Thereafter, a single colony was inoculated in LB medium (10 mL) containing the antibiotic, and cultured at 31° C. for 5 hours, and then was diluted 100-fold in Erlenmeyer flask (100 mL) containing seed medium (200 mL) of the L-methionine precursors. Additionally upon culturing of the same at 31° C. at a rate of 200 rpm for 3 hours to 10 hours, the seed culture broth was then inoculated in the fermenter (5 L) and cultured for 50 hours to 100 hours using a fermentation method of the fed-batch. The composition of main fermentation culture medium producing L-methionine precursors is shown in Table 1 below.

TABLE 1

Composition of fermentation medium producing L-methionine precursors

| Composition | Seed medium | Main medium | Feed medium |
|---|---|---|---|
| Glucose (g/L) | 10.1 | 40 | 600 |
| $MgSO_4 \cdot 7H_2O$ (g/L) | 0.5 | 4.2 | |
| Yeast extract (g/L) | 10 | 3.2 | |
| $KH_2PO_4$ | 3 | 3 | 8 |
| Ammonium sulfate (g/L) | | 6.3 | |
| $NH_4Cl$ (g/L) | 1 | | |
| NaCl (g/L) | 0.5 | | |
| $Na_2HPO_4 \cdot 12H_2O$ (g/L) | 5.07 | | |
| DL-Methionine (g/L) | | 0.5 | 0.5 |
| L-Isoleucine (g/L) | 0.05 | 0.5 | 0.5 |
| L-Threonine (g/L) | | 0.5 | 0.5 |

Example 1-2. L-Methionine Conversion Reaction

The fermentation culture medium produced from Example 1 was filtered using the membrane filtration so that O-acetyl homoserine culture medium and cells were separated. The liquid passed the same using the film (0.1 μm) is named permeate, which is the cell-free liquid. Additionally, the cell sludge was named as retentate.

The remaining O-acetyl homoserine in the retentate was re-collected by adding deionized water.

In order to carry out the enzyme conversion reaction, O-acetyl homoserine sulfhydrylase or *Rhodobacter sphaeroides*-derived O-acetylhomoserine sulfhydrylase, which is a L-methionine conversion enzyme, (Korean Patent No. 10-1250651), and methyl mercaptan was added to the permeate as a form of strain including an enzyme having an O-acetylhomoserine sulfhydrylase activity or the enzyme above.

The reaction was terminated when the concentration of the O-acetyl homoserine was no longer measured, by conducting the enzyme conversion reaction for 6 hours, and this reaction was conducted by measuring the concentration of the remaining O-acetyl homoserine, and supplying the methyl mercaptan during the reaction.

Example 1-3. Crystallization Process of L-Methionine

There is no any problem to use the L-methionine conversion fluid itself. However, in order to obtain the composition with the high content of L-methionine, a crystal may be separated by concentrating the conversion fluid of the L-methionine prepared in Examples 1 and 2, or a crystal may be concentrated with sulfuric acid upon adjustment of its pH to 4.0 to 5.5. In order to obtain the higher purity of the L-methionine, in this Example, sulfuric acid was added to adjust the pH to 4.0 to 5.5, and then an active carbon of 0.5 wt. % to 2 wt. % of the total amount in the L-methionine was further added to mix at 50° C. for 1 hour to 2 hours. Thereafter, the active carbon and impurities were removed upon filtration of the same. The filtrate was concentrated until the concentration of the L-methionine reached from 150 g/L to 200 g/L, and the crystal was then obtained using a crystal separation apparatus. The mother liquor obtained from the separation of the crystal was then concentrated once more in order to acquire a second crystal. Additionally, the second crystal was dissolved, and the dissolved crystal then re-added to a reaction liquid of the L-methionine which its pH had been adjusted to between 4.0 and 5.5. Additionally, the process above was repeated for use. Accordingly, 95.0 wt. % to 99.9 wt. % of the L-methionine was obtained.

Example 2: Synthesis of N-Acetyl-L-Methionine Using Chemical Synthesis Method

The L-methionine (20 g, 0.134 mol) prepared from Example 1 was placed in a flask (250 mL) upon mixing of the same with acetyl acetate (30 g), and an L-methionine solution in the condition of a suspension was prepared by stirring the solution in the flask (250 mL). When L-methionine particles were evenly dispersed after stirring the solution for 30 minutes, and concentrated sulfuric acid (0.133 g, 98.5%) and distilled water (0.666 g) were added, the above portion of the reactants is converted into a slurry state while white crystals extracted from the reactants. At this time, while continuing the stirring, the compound, such as acetic anhydride (14.4 g, 0.141 mol, and 97%) capable of acetylating an amine group of the L-methionine was slowly injected therein, and heat was applied to the flask equipped with a condensation tube. When the heat is applied while maintaining the temperature of the condensation tube below 0° C. using a chiller cooler, an evaporated acetyl acetate is refluxed into the flask through the condensation tube. At this moment, the temperature of the reactants was maintained at 83° C. When the reaction proceeded for 20 minutes, a color of the reactants in the slurry state slowly converted to have a clear-yellow liquid. At this time, the reactants were collected and rapidly cooled the same.

When the reaction products were strongly stirred for 1 hour to 2 hours, a white N-acetyl-L-methionine crystal was formed in a liquid. Additionally, when the white crystal was completely formed, the yellow supernatant was removed using a vacuum filter. The collected N-acetyl-L-methionine was washed using acetyl acetate which had been cooled at 0° C., and then, it was purified once more using the vacuum filter. Thereafter, the collected N-acetyl-L-methionine was dried using a decompression drying device under −0.1 Mpa at 50° C. for 1 hour. It was observed that the mass of the collected N-acetyl-L-methionine upon drying is 19.448 g (purified yields=77.8%), and also observed that the purity identified by HPLC analysis is 95.8%, and the purity of the remaining L-methionine is 0.6%.

Additionally, for evaluation of bio-derived content of the N-acetyl-L-methionine using the chemical synthesis method, the analysis was carried out based on the measuring method of the "bio-based content" in U.S. Pat. No. 8,946, 472. Further, the bio-based content was derived by using the formula below.

$$\text{Bio-Based Content} = {}^{14}C/{}^{12}C \text{ ratio sample}/{}^{14}C/{}^{12}C \text{ ratio modern}/1.075$$

The evaluated result of the mean the bio-based content in the N-acetyl-L-methionine produced by the chemical synthesis was observed to be 51.9%.

Example 3: N-Acetyl-L-Methionine Conversion of L-Methionine Based on Enzymatic Reaction N-acetyl-L-methionine conversion research was carried out based on enzymatic reaction using L-methionine.

In order to produce the N-acetyl-L-methionine by acetylating enzymatic reaction, *Pseudomonas putida*-derived N-acyltransferase (ppmat), *Bacillus subtilis*-derived N-acyltransferase (bsmat), *Enterobacter* sp. 638-derived N-acyltransferase (entmat), *Pseudovibrio* sp., FO-BEG1-derived N-acyltransferase (pvmat), *Yarrowia lipolytica*-derived N-acyltransferase (ylmat), *Corynebacterium glutamicum*-derived N-acyltransferase (cgmat), and *Escherichia coli*-derived N-acyltransferase (YncA) enzymes were used. The N-acyltransferase enzyme acted to pass an acetyl group from acetyl-CoA to a substrate. Such enzymatic reaction may be applied via enzymes such as, N-acetylglutamate synthase (ArgA), putative acetyltransferase (YjdJ), putative acetyltransferase (YfaP), putative acetyltransferase (YedL), and putative acetyltransferase (YjhQ), and further, may be applied with an enzyme having other ability of the acyltransferase in which the sequence-based homology is high.

Upon preparation of DNA fragments encoding the 7 types of the N-acyltransferase were prepared to have each of restriction enzyme site, of NdeI and XbaI at each end, respectively, the DNA fragments were ligated to a pUCtk vector treated with the same restriction enzymes. Upon transformation of the recombinant plasmid prepared above into *Escherichia coli* DH5a, the resultant was then plated on LB plate medium containing kanamycin, and cultured at 37° C. for overnight. After one of the obtained-colonies was inoculated in liquid LB medium (3 mL) containing kanamycin and then cultured for overnight, the recombinant plasmids were obtained using Plasmid Miniprep Kit (Bioneer, Korea). Sequence information of the obtained recombinant plasmids was confirmed by sequencing (Macrogen, Korea), and each recombinant plasmids were designated as pUCtk-ppmat, pUCtk-bsmat, pUCtk-entmat, pUCtk-pvmat, pUCtk-ylmat, pUCtk-cgmat, and pUCtk-yncA, respectively.

Transformed *Escherichia coli* BL21(DE3) in which the recombinant plasmids are introduced, was selected from LB plate medium containing kanamycin. The selected transformants were designated as BL21(DE3)/pUCtk-ppmat, BL21(DE3)/pUCtk-bsmat, BL21(DE3)/pUCtk-entmat, BL21(DE3)/pUCtk-pvmat, BL21(DE3)/pUCtk-ylmat, BL21(DE3)/pUCtk-cgmat, and BL21(DE3)/pUCtk-yncA, respectively.

One of each colonies of the prepared transformants, BL21(DE3)/pUCtk-ppmat, BL21(DE3)/pUCtk-bsmat, BL21(DE3)/pUCtk-entmat, BL21(DE3)/pUCtk-pvmat, BL21(DE3)/pUCtk-ylmat, BL21(DE3)/pUCtk-cgmat, and BL21(DE3)/pUCtk-yncA was inoculated in liquid LB medium (3 mL) containing kanamycin (25 mg/L) and 1% glucose (w/v), and cultured at 37° C. for 8 hours (seed culture). Thereafter, each seed culture broth was inoculated on the same medium (50 mL) and cultured for overnight.

The culture medium was centrifuged to obtain a pellet, and the resultant was suspended in phosphate buffer (pH 7.0, 50 mM, 5 mL), and then the cells were disrupted by sonication. The cell debris was removed by centrifugation at 14,000 rpm for 30 minutes to obtain a supernatant. Considering that the size of the acyltransferase is near 19 kDa, enzyme concentrate was obtained through the sequential filtration; a passing the Amicon Ultra (Millipore, Ireland) 30-kDa cut-off membrane, then re-filtrated through the 10-kDa cut-off membrane and remaining concentrate on the filter was obtained. The concentrate was filled in a HiTrap Q FF column (GE, USA) filled with Q sepharose, and the acyltransferase was purely separated using a NaCl concentration gradient (80, 100, 150, 200, 300, 500 mM sequence). A diluted enzyme was re-concentrated via Amicon Ultra 10-kDa cut-off membrane. The over-expression and purification degrees of the acyltransferase were confirmed using SDS-PAGE. In order to determine the productivity of the N-acetyl-L-methionine through the purified acyltransferase, the enzyme concentrate was added into a phosphate buffer (pH 7.0, 50 mM) containing acetyl-CoA (20 mM), and methionine (20 mM). After allowance of its reaction for 1 hour at 37° C., the amount of the produced N-acetyl-L-methionine was measured using HPLC.

TABLE 2

Production of N-acetyl-L-methionine through Novel acyltransferase Conversion Reaction

| Acyltransferase | N-acetyl-L-methionine concentration of conversion reaction solution (g/L) |
|---|---|
| BL21(DE3)/pUCtk-ppmat | 2.9 |
| BL21(DE3)/pUCtk-bsmat | 1.4 |
| BL21(DE3)/pUCtk-entmat | 1.9 |
| BL21(DE3)/pUCtk-pvmat | 0.5 |
| BL21(DE3)/pUCtk-ylmat | 0.3 |
| BL21(DE3)/pUCtk-cgmat | 1.1 |
| BL21(DE3)/pUCtk-yncA | 1.3 |

From the results above, it was observed that L-methionine is converted into N-acetyl-L-methionine by the acyltransferase. The conversion reaction is not only possible with L-methionine diluted in a buffer solution, but also possible with L-methionine which is not purified in a culture medium produced from fermentation and enzymatic conversion reaction. On the other hand, a metabolic engineering approach is possible through the addition of glucose or acetic acid in order to supply a sufficient amount of acetyl-CoA in the acyltransferase-producing bacteria, and the production yield of the N-acetyl-L-transferase can be ameliorated by improving a fermentation process.

The Examples of the N-acetylating method using the bio-based L-methionine should be understood as illustrative, and is not intended to limit the present disclosure. That is, a method for producing bio-based N-acetyl-L-methionine of the present disclosure is to produce L-methionine in high yield by fermenting bio-based raw materials, and to prepare N-acetyl-L-methionine using an easy and simple way through various acetylating processes. The Examples above are representatively carried out the same.

Example 4: Production of N-Acetyl-L-Methionine Using N-Acyltransferase-Introduced Transformant One of each colonies in the transformants BL21(DE3)/pUCtk-ppmat, BL21(DE3)/pUCtk-bsmat, BL21(DE3)/pUCtk-entmat, BL21(DE3)/pUCtk-pvmat, BL21(DE3)/pUCtk-ylmat, BL21(DE3)/pUCtk-cgmat, and BL21(DE3)/pUCtk-yncA, which were prepared in Example 3, was inoculated in liquid LB medium (3 mL) containing kanamycin (25 mg/L), and 1% glucose (w/v), and cultured at 37° C. for 8 hours. Thereafter, the culture medium (500 µl) was inoculated into liquid LB medium (50 mL) containing kanamycin (25 mg/L), 1% glucose (w/v), and 2% methionine (w/v), and then cultured for overnight. A pUCtk vector, in which a target gene is not inserted, was transformed to be used as a control. Cells in the culture medium were removed through centrifugation, and then the produced N-acetyl-L-methionine was analyzed using HPLC.

As a result, BL21(DE3)/pUCtk-ppmat produced N-acetyl-L-methionine with the highest concentration of 3.03 g/L, and BL21(DE3)/pUCtk-entmat produced the N-acetyl-L-methionine with the second highest concentration of 2.23 g/L. A trace amount of the N-acetyl-L-methionine was detected in the control, and it was assumed that the N-acetyl-L-methionine in the control was produced by YncA enzyme which is inherently expressed in *Escherichia coli*. Additionally, it was observed that, when YncA was over-expressed in a wild-type *Escherichia coli*, the productivity of the N-acetyl-L-methionine was increased, in comparison with that of the control (Table 3).

TABLE 3

Ability to produce N-acetyl-L-methionine of *Escherichia coli* transformed into acyltransferase

| Transformant | N-acetyl-L-methionine concentration of culture medium (g/L) |
| --- | --- |
| BL21(DE3)/pUCtk | <0.1 |
| BL21(DE3)/pUCtk-ppmat | 3.03 |
| BL21(DE3)/pUCtk-bsmat | 1.60 |
| BL21(DE3)/pUCtk-entmat | 2.23 |
| BL21(DE3)/pUCtk-pvmat | 0.17 |
| BL21(DE3)/pUCtk-ylmat | 0.13 |
| BL21(DE3)/pUCtk-cgmat | 0.58 |
| BL21(DE3)/pUCtk-yncA | 1.15 |

Additionally, for evaluation of bio-derived content of the N-acetyl-L-methionine produced with a basis of transformed *Escherichia coli*, the analysis was carried out based on the measuring method of the "bio-based content" in U.S. Pat. No. 8,946,472. As a result of the evaluation, the mean bio-based content of the N-acetyl-L-methionine produced by the transformed *Escherichia coli* was confirmed to be 76.6%.

Accordingly, it was confirmed that the L-methionine can be acetylated by a chemical synthesis process, an acetylating enzyme, or a microorganism producing the same, and particularly, was confirmed that the environmentally friendly production with high efficiency of the bio-based N-acetyl-L-methionine is possible by acetylating enzymatic reaction.

Example 5: Production of N-Acetyl-L-Methionine Via Fermentation of Transformed L-Methionine Producing Strains Example 5-1. Direct Fermentation Using Strains Producing L-Methionine and Enzymatic Conversion Effect Thereof An Erlenmeyer flask culture was carried out in order to produce L-methionine using *Escherichia coli* TF4076BJF metA #10+metYX (Lm) (Korean Patent No. 10-1140906; hereinafter, metA10YXLm), as strains producing L-methionine. The strains were inoculated on LB plate medium, and were cultured at 31° C. for overnight. A formed single colony was then inoculated in seed medium (10 mL), and was cultured at 31° C. for 6 hours. Thereafter, the seed culture medium (1 mL) was inoculated in an Erlenmeyer flask (250 mL) containing main fermentation medium (20 mL), and cultured at 31° C. at 200 rpm for 78 hours. The composition of the seed medium and main fermentation medium is described in Table 4 below.

TABLE 4

| Composition (g/L) | Seed medium (seed media) | Main medium (main media) |
| --- | --- | --- |
| Glucose | 2 | 40 |
| MgSO$_4$•7H$_2$O | 0.49 | 1 |
| Yeast extract | 10 | 2 |
| KH$_2$PO$_4$ | 3 | 2 |
| Ammonium sulfate |  | 17 |
| CaCl$_2$•2H$_2$O | 0.015 |  |
| CaCO$_3$ |  | 30 |
| NaCl | 0.5 |  |
| Na$_2$HPO$_4$•12H$_2$O | 6 |  |
| MnSO$_4$•7H$_2$O |  | 0.01 |
| FeSO$_4$•7H$_2$O |  | 0.01 |
| ZnSO$_4$•7H$_2$O |  | 0.01 |
| L-Threonine |  | 0.3 |

As a result of analysis using the concentration of L-methionine in culture medium, 6.6 g/L of the L-methionine was produced.

Additionally, the production of N-acetyl-L-methionine was carried out using acyltransferase with L-methionine produced directly by the fermentation of L-methionine producing strains. The evaluation was carried out by applying purified acyltransferase obtained by a method corresponding to that of Example 3, and the experiment was carried by using the L-methionine in the culture medium obtained by the direct fermentation. That is, acetyl-CoA (20 mM) and direct fermentation culture medium of L-methionine were mixed with phosphate buffer (pH 7.0, 50 mM), and enzyme concentrate was added therein. Thereafter, the mixed L-methionine solution was reacted at 37° C. for 1 hour, and an amount of N-acetyl-L-methionine produced therefrom was measured using HPLC, and the experimental results are as follows.

TABLE 5

Ability to produce N-acetyl-L-methionine by conversion reaction of acyltransferase based on culture medium directly fermenting L-methionine

| Acyltransferase | Concentrations of N-acetyl-L-methionine produced via culture medium directly fermenting L-methionine (g/L) |
| --- | --- |
| BL21(DE3)/pUCtk-ppmat | 3.73 |
| BL21(DE3)/pUCtk-bsmat | 1.92 |
| BL21(DE3)/pUCtk-entmat | 2.87 |
| BL21(DE3)/pUCtk-pvmat | 0.75 |
| BL21(DE3)/pUCtk-ylmat | 0.39 |
| BL21(DE3)/pUCtk-cgmat | 1.23 |
| BL21(DE3)/pUCtk-yncA | 1.63 |

Although the ability to produce N-acetyl-L-methionine was evaluated for culture medium of L-methionine produced from direct fermentation in Example above, the production of the N-acetyl-L-methionine is also possible using a purified powder of the L-methionine produced by the direct fermentation corresponding to Example 3.

Example 5-2. Production of N-Acetyl-L-Methionine by Fermentation of Transformants Derived from Strains Directly Producing L-Methionine in which N-Acyl-Transferase is Introduced (Strains Directly Producing N-Acetyl-L-Methionine)

The direct production of N-acetyl-L-methionine via fermentation was attempted by utilizing *Escherichia coli* TF4076BJF metA #10+metYX (Lm) (Korean Patent No.

10-1140906; hereinafter, metA10YXLm), as strains producing L-methionine. The recombinant plasmids, pUCtk-ppmat, pUCtk-bsmat, pUCtk-entmat, pUCtk-pvmat, pUCtk-ylmat, pUCtk-cgmat, and pUCtk-yncA prepared from Example 3, are respectively introduced, and the transformants derived from transformed *Escherichia coli* metA10YXLm were selected from LB plate medium containing kanamycin. The selected transformants were designated as metA10YXLm/pUCtk-ppmat, metA10YXLm/pUCtk-bsmat, metA10YXLm/pUCtk-entmat, metA10YXLm/pUCtk-pvmat, metA10YXLm/pUCtk-ylmat, metA10YXLm/pUCtk-cgmat, and metA10YXLm/pUCtk-yncA, respectively. The culture and analysis of the transformed strains were carried out based on the fermentation conditions described in Example 5-1. As a result of the analysis, metA10YXLm/pUCtk-ppmat produced N-acetyl-L-methionine with the highest concentration of 8.32 g/L, while metA10YXLm/pUCtk-entmat produced N-acetyl-L-methionine with the second highest concentration of 6.19 g/L (Table 6).

Additionally, in order to improve the direct production of N-acetyl-L-methionine, a comparative evaluation of the prepared transformants was carried out by supplying additional L-methionine from an outside source. In order for this, 2% of L-methionine was additionally added in the fermentation conditions. It was confirmed from the analysis result that the production of N-acetyl-L-methionine of the transformants were increased, and particularly, was confirmed that the metA10YXLm/pUCtk-ppmat strains, which had exhibited the highest production of N-acetyl-L-methionine without an addition of L-methionine, also exhibits the highest production of N-acetyl-L-methionine (14.1 g/L) (Table 6). With such result, the increased amount of production can be expected when N-acetyl-L-methionine is produced using the strains in which the ability to produce L-methionine is further improved, and at the same time, the increased production of N-acetyl-L-methionine also can be expected by additionally supplying L-methionine from an outside source. In particular, a wild-type *Escherichia coli* has an inherent YncA enzyme, and thus exhibits the trace amount of production of N-acetyl-L-methionine (Example 4). However, it was confirmed that the strains producing N-acetyl-L-methionine, in which the ability to produce L-methionine is increased, exhibits the increased production of N-acetyl-L-methionine in the control. It is believed that such increased production is due to L-methionine produced in the strains, or due to L-methionine supplied from an outside source.

TABLE 6

Ability to produce N-acetyl-L-methionine of acyltransferase-transformed strains directly producing N-acetyl-L-methionine

| Transformant | N-acetyl-L-methionine concentration of culture medium (g/L) | |
| --- | --- | --- |
|  | Non-addition of external L-methionine | Addition of external L-methionine |
| metA10YXLm/pUCtk | 0.11 | 0.25 |
| metA10YXLm/pUCtk-ppmat | 8.32 | 14.1 |
| metA10YXLm/pUCtk-bsmat | 4.17 | 7.35 |
| metA10YXLm/pUCtk-entmat | 6.19 | 10.9 |
| metA10YXLm/pUCtk-pvmat | 0.76 | 1.33 |
| metA10YXLm/pUCtk-ylmat | 0.39 | 0.69 |

TABLE 6-continued

Ability to produce N-acetyl-L-methionine of acyltransferase-transformed strains directly producing N-acetyl-L-methionine

| Transformant | N-acetyl-L-methionine concentration of culture medium (g/L) | |
| --- | --- | --- |
|  | Non-addition of external L-methionine | Addition of external L-methionine |
| metA10YXLm/pUCtk-cgmat | 2.02 | 3.12 |
| metA10YXLm/pUCtk-yncA | 3.18 | 5.29 |

Additionally, for evaluation of bio-derived content of the N-acetyl-L-methionine produced using the direct fermentation, the analysis was carried out based on the measuring method of the "bio-based content" in U.S. Pat. No. 8,946,472. It was confirmed from the evaluation result that the mean bio-based content of the N-acetyl-L-methionine produced using the direct fermentation is 99.3%.

Example 6: Bypass Efficiency Test of Bio-Based N-Acetyl-L-Methionine by In Vitro Fermentation of Ruminal Microflora 6-1. Collection of Ruminal Fluid One Holstein steer (weighing around 630 kg to 650 kg) equipped with ruminal cannula was provided for an experimental purpose, and the Holstein steer was bred by feeding the commercial feed (Milkgen™, CJ CheilJedang) and rice straws twice a day (7:30 a.m., 3:00 a.m.).

The collection of ruminal fluid was carried out at 10 a.m. on the experimental day. Contents in the rumen were removed through a cannula, and gastric fluid was extracted with gauze by squeezing the same. Thereafter, the extracted gastric fluid was placed in a vacuum flask, and bubbled with $CO_2$. The vacuum flak containing the gastric fluid was then carried to a laboratory while blocking a penetration of oxygen. It took less than an hour to carry the ruminal fluid to the laboratory.

6-2. Progress of Anaerobic Culture

The ruminal fluid carried to the laboratory was filtered with two layers of gauze, and then it was used as anaerobic culture medium by mixing the same with a biomimetic solution of McDougall's buffer (Troelsen and Donna, 1966), which is commonly used in the in vitro rumen bypass test, in a ratio of 1:3. The composition of the biomimetic solution of the McDougall's buffer is as shown in Table 7 below.

TABLE 7

Composition of biomimetic solution of McDougall's buffer Buffer (based on 1 L)

| $NaH_2PO_4 \cdot 2H_2O$ | 9.3 g |
| --- | --- |
| $NaHCO_3$ | 9.8 g |
| NaCl | 0.47 g |
| KCl | 0.57 g |
| $MgCl_2$ | 0.256 g |
| $CaCl_2$ | 0.106 g |
| EZMIX N-ZAMIN | 2.5 g |
| resazulin (0.1%) | 1.5 ml |

A feed used in the experiment was the commercial feed (Milkgen™), a feed substantially used for cattle breeding, and the feed was also used as a basal diet. Further, the experimental samples were prepared by mixing the basal diet with a test material. The test material used in this experiment was N-acetyl-L-methionine, and this was used as an experimental group 1. The experimental group 1 was compared with the control group 1 composed of only the basal diet without the test material, and also compared with the control group 2 composed of the test material, L-methionine. The culture was carried out with three replications for each experimental group.

The basal diet and test material were mixed in a ratio of 4:1 (basic diet (0.4 g), test material (0.1 g); but only 0.5 g of basic diet in control group 1). The culture initiated when the mixed test material (0.5 g) was added in a culture bottle (125 mL), and then mixed it with the prepared anaerobic culture medium (50 mL), and placed in 40° C. incubator upon sealing of the same.

$O_2$ free $CO_2$ was sprayed during the entire process including dilution of the ruminal fluid until the initiation of the culture, so that the ruminal fluid was not exposed to oxygen. Therefore, the anaerobic condition was maintained.

6-3. Sampling and Result of Measuring In Vitro Rumen Bypass Efficiency of Test Material The culture was finally carried out for 48 hours, and sampling of the culture medium was carried out a total of four times (0 h, 24 h, 36 h, 48 h) upon the initiation of the culture. At each sampling, the sample placed in the 40° C. incubator was moved from the incubator and opened its lid. Thereafter, a supernatant was obtained by centrifuging the culture medium at 4000 rpm for 10 minutes, and then the amount of the test material present in the supernatant was measured.

Based on the results of HPLC quantitative analysis of the test material, the rate (%) of rumen bypass was calculated, and the calculated values are shown in Table 8 below.

TABLE 8

Rate of in vitro rumen bypass of N-acetyl-L-methionine (%)
Rate of rumen bypass (%)

| | 0 hour | | | | | 24 hours | | | | |
|---|---|---|---|---|---|---|---|---|---|---|
| | 1 | 2 | 3 | Average | SD | 1 | 2 | 3 | Average | SD |
| Control group 2(L-methionine) | 100 | 100 | 100 | 100 | 0.0 | 51.2 | 62.6 | 62.7 | 58.8 | 6.7 |
| Experimental group 1(N-acetyl-L-methionine) | 100 | 100 | 100 | 100 | 0.0 | 87.5 | 90.5 | 89.4 | 89.1 | 1.5 |

| | 36 hours | | | | | 48 hours | | | | |
|---|---|---|---|---|---|---|---|---|---|---|
| | 1 | 2 | 3 | Average | SD | 1 | 2 | 3 | Average | SD |
| Control group 2(L-methionine) | 29.4 | 42.3 | 36.2 | 36.0 | 6.5 | 1.9 | 1.5 | 0.9 | 1.5 | 0.5 |
| Experimental group 1(N-acetyl-L-methionine) | 72.5 | 80.1 | 76.0 | 76.2 | 3.8 | 52.6 | 57.2 | 56.5 | 55.4 | 2.5 |

Figure 1:
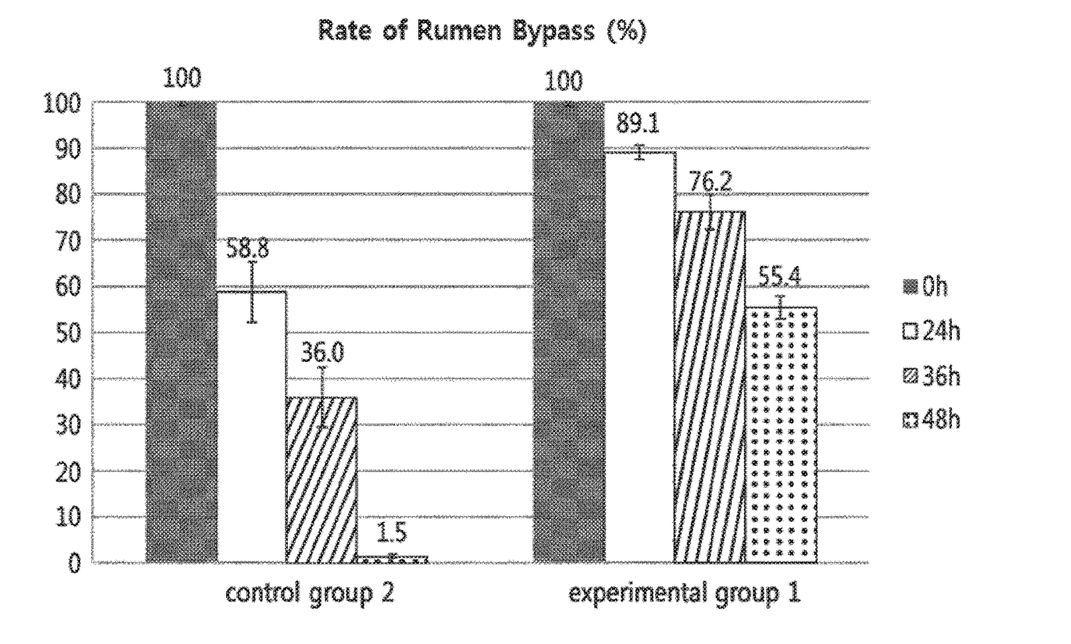
The FIGURE is a graph showing the rumen bypass rate (%) of N-acetyl-L-methionine.

The bypass rate (%) is represented as a residual amount (%) at time-points of 24 hours, 36 hours, and 48 hours, based on the amount of a test material at the time-point of 0 hour (100%). FIG. 1 shows rate of rumen bypass (%).

As a result, the control group L-methionine exhibits that the rate (%) of rumen bypass after 48 hours was 1.5%, compared to the rate at the time-point of 0 hour, and thus it was confirmed that most were digested by microorganisms in the rumen. Additionally, the test material N-acetyl-L-methionine exhibits the rate (%) of rumen bypass after 24 hours as 89.1%, after 36 hours as 76.2%, and even after 48 hours as 55.4%, compared to the rate at the time-point of 0 hour.

Example 7: Experiment for Measuring Digestibility of Bio-Based N-Acetyl-L-Methionine Through Extracts of In Vitro Small Intestine and Liver Nutrients which did not degraded by microorganisms in the rumen are absorbed in the small intestine so that can be used for protein synthesis, energy metabolism, etc. For the N-acetyl-L-methionine, it is expected to reach the small intestine with high bypass rate. Accordingly, it can be converted into methionine by digestive enzyme existing in the small intestine and liver to the same, and therefore, can be easily absorbed in the small intestine of ruminants. For this reason, enzymes existing in the bovine small intestine and liver were subjected to observe the potential digestive degradation of the N-acetyl-L-methionine.

Example 7-1. Obtaining Extracts from Small Intestine

The small intestine (40 m) of Korean native cattle (record number: KOR005078680400), slaughtered in Bucheon livestock products market of National Agricultural Cooperative Federation, was purchased. After slicing the small intestine to around 1 m, 20 mM sodium phosphate buffer (pH 7.4, 5 mL) was added in the sliced small intestine. Thereafter, while holding each ends of the small intestine, the small intestine was repeatedly waggled to help most of enzymes in the small intestine to be dissolved by the sodium phosphate buffer. By doing this, approximately 200 mL of enzyme solution were obtained from the small intestine (40 m), and supernatants were obtained by centrifuging at 4° C. at 14,000 rpm for 10 minutes, and then the resultants were diluted 2-fold in the 20 mM sodium phosphate buffer (pH 7.4).

Example 7-2. Obtaining Extracts from Liver

The liver of Korean native cattle (record number: KOR005078680400), slaughtered in Bucheon livestock products market of National Agricultural Cooperative Federation, was purchased. After mixing liver tissues (0.125 g) with 20 mM sodium phosphate buffer (pH 7.4, 1 mL), glass beads (Sigma G1145) were filled in about ⅒ of a tube (2 mL). The cell tissues were disrupted using a beadbeater (MP™ FastPrep) for three times with each 20 seconds, and the resultant was centrifuged at 4° C. at 14,000 rpm for 10 minutes to obtain supernatants.

Example 7-3. Evaluation of Enzymatic Activity of Extracts Obtained from Small Intestine and Liver To confirmed the enzymatic activity of the extracts obtained from small intestine and liver, acylase I (sigma A3010) extracted from pig kidney was used. It is known that N-acetyl-L-methionine can be degraded well by acylase I (Chem. Res. Toxicol. 1998, 11(7):800-809). Through the comparison of the relative activity with the acylase I, the digestive degradation rate of the N-acetyl-L-methionine by the extracts of the small intestine and liver was observed. Experimental conditions are the same as shown in Table 9 below, and the reaction was carried out at 40° C. for 24 hours.

TABLE 9

Evaluation conditions of digestive degradation rate of N-acetyl-L-methionine by extracts of bovine small intestine and liver

|  | Acylase I (1 mg/ml) | Extracts of small intestine | Extracts of liver |
| --- | --- | --- | --- |
| N-ACETYL-L-METHIONINE (4 g/L) | 500 | 500 | 500 |
| Acylase I (1 mg/ml) | 100 | | |
| Extracts of small intestine (diluted 2-fold) | | 100 | |
| Extracts of liver | | | 100 |
| 20 mM Sodium phosphate buffer (pH 7.4) | 400 | 400 | 400 |
| Final reacted volume (μl) | 1000 | 1000 | 1000 |

In order to remove protein in the sample which the reaction was over, perchloric acid (0.5%) was added therein and diluted 10-fold. Thereafter, the N-acetyl-L-methionine and L-methionine existing in the supernatant, which is separated by centrifugation at 14,000 for 10 minutes, were quantitatively analyzed (HPLC). Conversion rate (%) was calculated by comparing the molar concentrations (mM) between the N-acetyl-L-methionine prior to the reaction and the L-methionine after the reaction, in terms of the percentage (%) (the molecular weight of the N-acetyl-L-methionine: 191.25 g/L; and the molecular weight of the L-methionine: 149.25 g/L).

As a result of the analysis, it was observed that acylase I exhibits high digestive degradation rate (98.9%, mol conversion rate), which is similar to the rate in the literature. Similarly, it was also observed that the reaction using the small intestine extracts (97.5% mol conversion rate) and the reaction using the liver extracts (99.1% mol conversion rate) exhibit very high digestive degradation rate.

TABLE 10

Digestive degradation rate of N-acetyl-L-methionine by acylase I, and extracts of small intestine and liver

|  | N-ACETYL-L-METHIONINE (mM) | L-methionine (mM) | Digestive degradation rate (%) |
| --- | --- | --- | --- |
| Acylase I (0.1 mg/ml) | 11.4 | 11.1 | 98.9 |
| Extracts of small intestine | 11.2 | 10.9 | 97.5 |
| Extracts of liver | 11.2 | 11.1 | 99.1 |

* Digestive degradation rate: producing material (methionine) mM concentration/substrate (N-acetyl-L-methionine) mM concentration × 100

As a result, from Example above, N-acetyl-L-methionine was converted into L-methionine in in vitro reaction of extracts of the small intestine and liver. From this result, when N-acetyl-L-methionine reached the small intestine, most of the N-acetyl-L-methionine converted into L-methionine by the digestive enzymes in the small intestine, and it can be anticipated that a trace amount of undegraded N-acetyl-L-methionine is absorbed in the small intestine, flowed into the liver via the blood, and converted to L-methionine. It signifies that N-acetyl-L-methionine provided as a feed additive may be directly utilized as L-methionine, which is substantially used as an amino acid in the body of ruminants.

Example 8: Comparative Evaluation of In Vitro Digestive Degradation Rate of N-Acetyl-L-Methionine and N-Acetyl-D,L-Methionine by the Extracts of Small Intestine and Liver

Example 8-1. Evaluation for Digestive Degradation Rate by Extracts of Small Intestine and Liver Comparative evaluation of digestive degradation rate according to optical isomers of N-acetyl-L-methionine was carried out using the extracts of the small intestine and liver obtained from Example 7. The evaluation was progressed in the same manner as shown in Example 7-3, and the evaluation results are as follows.

TABLE 11

Digestive degradation rate of N-acetyl-L-methionine and N-acetyl-D,L-methionine by extracts of small intestine and liver

|  | N-ACETYL-L-ME-THIONINE (mM) | L-me-thionine (mM) | Digestive degradation rate (%) | N-acetyl-D,L-me-thionine (mM) | L-me-thionine (mM) | Digestive degradation rate (%) |
|---|---|---|---|---|---|---|
| Extracts of small intestine | 11.2 | 10.9 | 97.50 | 12.7 | 5.82 | 45.82 |
| Extracts of liver | 11.2 | 11.1 | 99.10 | 12.7 | 6.36 | 50.08 |

In in vitro reaction of the extracts of the small intestine and liver, approximately 46% of N-acetyl-D,L-methionine containing approximately 50% of D-form was converted into L-methionine by the extracts of the small intestine, whereas approximately 50% of the N-acetyl-D,L-methionine was converted into L-methionine by the extracts of the liver. That is, in the body, the digestive degradation rate of N-acetyl-L-methionine (L-form) is significantly high in comparison with N-acetyl-D-methionine (D-form) among the optical isomers. Additionally, from the results above, it can be anticipated that it exhibits significantly low digestive degradation rate when N-acetyl-D,L-methionine is used, contrast the digestive degradation rate when the same amount of N-acetyl-L-methionine is used.

Example 9: Analysis of Milk Composition Through Feeding N-Acetyl-L-Methionine Based on the in vitro evaluation, the N-acetyl-L-methionine, for which high digestive degradation rate in the small intestine and bypass rate in the rumen had been observed, was subjected to verify its efficiency through a substantial evaluation with dairy cows. In order for this, the cows were divided into two separated groups, and the change in milk composition depending on presence or absence of the N-acetyl-L-methionine was analyzed during the evaluation. For this, eight dairy cows were divided into two groups so that each group consists of four cows, respectively. Additionally, the N-acetyl-L-methionine was added to the feed composition (Table 12) which are fed by the four cows in one group (30 g of N-acetyl-L-methionine by each cow per a day), and it was carried out for 84 days.

Group 1: Non-addition of N-acetyl-L-methionine
Group 2: Addition of N-acetyl-L-methionine

TABLE 12

Feed composition

| Feed ingredient (% of DM) | Non-addition of N-acetyl-L-methionine | Addition of N-acetyl-L-methionine |
|---|---|---|
| Alfalfa hay | 25.8 | 25.7 |
| Wheat straw | 2.38 | 2.38 |
| Corn silage | 31.0 | 31.0 |
| Corn, steam-flaked | 11.1 | 11.1 |
| Corn, high moisture | 5.90 | 5.89 |
| Cottonseed, whole | 4.66 | 4.65 |
| Canola meal | 5.68 | 5.68 |
| Soybean meal | 5.27 | 5.27 |
| Beet pulp, shreds | 4.71 | 4.70 |
| N-acetyl-L-methionine | — | 0.13 |
| Sodium bicarbonate | 1.03 | 1.03 |
| Vitamin and mineral mix 2 | 2.43 | 2.42 |

The analysis results of milk composition of tested dairy cows are shown in Table 13 below.

TABLE 13

Results of milk production and composition

| | Main items | Non-addition of N-acetyl-L-methionine | Addition of N-acetyl-L-methionine | Rate of increase (%) |
|---|---|---|---|---|
| | Amount of feed intake (DMI), kg/d | 25.4 | 25.4 | 0.0 |
| Amount of production (kg/d) | 3.5% FCM (Fat-corrected milk) | 40.4 | 43.4 | 7.4 |
| | ECM (Energy-corrected milk) | 40.2 | 42.9 | 6.7 |
| Rate of milk ingredients, % | Milk fat | 3.34 | 3.70 | 10.8 |
| | Milk protein | 2.78 | 2.83 | 1.8 |
| Production of milk ingredients, kg/d | Milk fat | 1.39 | 1.56 | 12.2 |
| | Milk protein | 1.14 | 1.18 | 3.5 |
| Feed efficiency | Milk production/Feed intake (Milk yield/DMI) | 1.61 | 1.66 | 3.1 |
| | 3.5% FCM yield/DMI | 1.57 | 1.72 | 9.6 |
| | ECM yield/DMI | 1.57 | 1.70 | 8.3 |

As shown in the specification evaluation above, the change in the total feed intake (dry matter intake, DMI) in accordance with presence or absence of the N-acetyl-L-methionine was not observed. However, an increase in the milk fat (12.2%) and milk protein (3.5%) was observed with the addition of the N-acetyl-L-methionine. Additionally, 6.7% was increased for the energy-corrected milk (ECM), in comparison with that without the addition of the N-acetyl-L-methionine. Further, the feed efficiency (ECM yield/DMI) was also increased by 8.3%. That is, as can be seen from the results above, various effects, such as the increase in the fat and protein contents in the milk, and the increase in feed efficiency, were observed with the addition of N-acetyl-L-methionine as feed additive for dairy cows.

Example 10: Analysis of Weight Gain Effect Through Feeding N-Acetyl-L-Methionine The weight gain effect of beef steers was verified through feeding N-acetyl-L-methionine. For the verification, 24 beef steers were divided into two groups so that each group consisted of 12 beef steers. Thereafter, the weight gain effect in accordance with presence or absence of N-acetyl-L-methionine was observed for 90 days. In the group with the addition of N-acetyl-L-methionine, each beef steer was fed with the N-acetyl-L-methionine (30 g) per a day.

Basic feed compositions are the same as shown in Table 12, and the weight gain effect by the evaluation is as follows.

TABLE 14

Results of weight gain effect

| Main items | | Non-addition of N-acetyl-L-methionine | Addition of N-acetyl-L-methionine | Rate of increase (%) |
|---|---|---|---|---|
| Weight of beef steer (kg) | Before feeding | 252.7 | 249.2 | — |
| | 3 months after feeding | 369.1 | 382.1 | — |
| | Weight gain (kg) | 116.4 | 132.9 | 14.2 |
| | Average daily weight gain (kg/d) | 1.29 | 1.48 | 14.7 |

As can be observed from the evaluation of the beef steer, approximately 132.9 kg of a weight gain effect was observed when the N-acetyl-L-methionine was further fed to the beef steer, and this corresponds to additional weight gain of 16.5 kg in comparison with one without the N-acetyl-L-methionine. Additionally, the average daily weight gain also shows an improved effect by approximately 14.7% in comparison with one without the addition of N-acetyl-L-methionine. That is, various effects, such as the increase in the fat and protein contents in dairy cows' milk, and the increase in feed efficiency, are not only observed by applying the feed additive of the N-acetyl-L-methionine (Example 9), but also the improved effect of gaining weight in beef steers were observed, from the results above. Based on these results, the possibility of the N-acetyl-L-methionine to be used as a feed additive of various ruminants was confirmed.

Example 11: Preparation for Fermentation Culture Medium of Bio-Based N-Acetyl-L-Methionine Example 11-1. Preparation for Fermentation Culture Medium of N-Acetyl-L-Methionine Using *Corynebacterium glutamicum*

In this Example, *Corynebacterium glutamicum* (ATCC13032) having an inherent ability to produce N-acetyl-L-methionine was cultured in L-methionine-containing medium (1 L) (composition (based on 1 L): L-methionine (20 g), glucose (20 g), peptone (10 g), yeast extracts (10 g), urea (5 g), $KH_2PO_4$ (4 g), $K_2HPO_4$ (8 g), $MgSO_4 \cdot 7H_2O$ (0.5 g), biotin (100 μg), thiamine HCl (1,000 μg)) in the range of pH of 6.0 to 8.0 at 35° C. for 72 hours. Therefore, the fermentation culture medium, in which the concentration of the N-acetyl-L-methionine is 1.07 g/L, was obtained.

Example 11-2. Preparation of Fermentation Culture Medium of N-Acetyl-L-Methionine Using *Yarrowia lipolytica*

In this Example, *Yarrowia lipolytica* PO1f (ATCC MYA-2613TM) having an inherent ability to produce N-acetyl-L-methionine was cultured in L-methionine-containing medium (1 L) (composition (based on 1 L): L-methionine (20 g), glucose (20 g), $Na_2HPO_4$ (3.28 g), $NaH_2PO_4$ (3.22 g), yeast extracts (2 g), Proteose-peptone (50 g)) in the range of pH 6.0-8.0 at 30° C. for 72 hours. Therefore, the fermentation culture medium, in which the concentration of the N-acetyl-L-methionine is 1.02 g/L, was obtained. For the medium containing L-methionine, it increases the production of the N-acetyl-L-methionine, and mother liquor of L-methionine produced from microorganism fermentation can be used.

Example 12: Direct Granulation from Fermentation Culture Medium

The fermentation culture medium or a filtrate thereof was concentrated to a total solid content of 40 wt. % to 60 wt. %, and the pH was adjusted to between 3.5 and 3.6. The pH adjustment was conducted using sulfuric acid, and after the pH adjustment, the concentrate was allowed to stand at 60° C. for 2.5 hours. After gDNA degradation process, the concentrate was injected into a granulator through a lower nozzle of the granulator (GR Engineering, Fluid Bed Spray Dryer Batch type Pilot), using the bottom-spraying method. Conditions for operating the granulator were as follows: heater temperature (170° C.), inlet temperature (140° C. to 160° C.), outlet temperature (60° C. to 70° C.), and spray pressure (1.8 bar to 2.0 bar). The seed for granulation was prepared by the spray-drying method, and the size thereof was 300 μm. The concentrate injected into the granulator was dried by a hot air, and then it was solidified. Thereafter, the size thereof increased by the newly injected concentrate while being flowed in the fluidized bed. When the size of the granule particle reached a desired size, the operation of the granulator was stopped, and the product was recovered for analyzing composition of the product and contents thereof.

The features of the granules of the *Corynebacterium glutamicum*-fermentation culture medium and granules of the *Yarrowia lipolytica*-fermentation culture medium obtained from this Example are shown in Table 15 below.

TABLE 15

| | Granules of *Corynebacterium glutamicum*-fermentation culture medium | Granules of *Yarrowia lipolytica*-fermentation culture medium |
|---|---|---|
| N-acetyl-L-methionine content | 50% | 40% |
| Protein content | 14% | 18% |
| Crude fat content | — | 10% |

TABLE 15-continued

| | Granules of Corynebacterium glutamicum-fermentation culture medium | Granules of Yarrowia lipolytica-fermentation culture medium |
|---|---|---|
| Moisture content | 2% | 2% |
| Apparent density | 665.1 kg/m$^3$ | 667.5 kg/m$^3$ |
| Inorganic compound content | 1.6% | 1% |
| Particle size less than or equal to 500 μm | 5% | 5% |
| Particle size greater than 500 μm, but less than or equal to 1000 μm | 28.6% | 24.6% |
| Particle size greater than 1000 μm, but less than or equal to 1300 μm | 63.4% | 66.4% |
| Particle size greater than 1300 μm | 3% | 4% |

Example 13. Content Adjustment by Adding Free N-Acetyl-L-Methionine into Fermentation Culture Medium Under the same condition as Example 11, the fermentation culture medium produced from the fermentation culture process was concentrated to a total solid content of 40 wt. % to 60 wt. %. Further, the free N-acetyl-L-methionine was added thereto in a mixing tank, and mixed. Thereafter, granules were formed according to the same conditions in Example 12.

The features of the product finally obtained using *Corynebacterium glutamicum* and *Yarrowia lipolytica* are shown in Table 16 below. Consequently, the granular products having increased protein and fat contents could be obtained.

TABLE 16

| | Final product obtained from granulation of Corynebacterium glutamicum | Final product obtained from granulation of Yarrowia lipolytica |
|---|---|---|
| N-acetyl-L-mthionine content | 66% | 55% |
| Protein content | 15% | 19.8% |
| Crude fat content | — | 12.8% |
| Moisture content | 0.5% | 0.12% |
| Apparent density | 665.5 kg/m$^3$ | 668.3 kg/m$^3$ |
| Inorganic compound content | 2.5% | 1.5% |
| Particle size less than or equal to 500 μm | 3% | 2% |
| Particle size greater than 500 μm, but less than or euqal to 1000 μm | 28% | 27% |
| Particle size greater than 1000 μm, but less than or equal to 1300 μm | 67% | 67% |
| Particle size greater than 1300 μm | 2% | 4% |

Example 14. Content Adjustment by Adding Diluting Agent to Fermentation Culture Medium After concentrating the fermentation culture medium, corn starch (0.22 kg) which is dissolved in 0.5 L of water and resulted in having 9.0% of moisture content, were added in a mixing tank as a diluting agent, and then mixed. A filtrate of the fermentation culture medium was concentrated to a total solid content of 50.5 wt. % by a method of concentrating under reduced pressure, and granules were formed according to the same conditions in Example 12.

The features of the product finally obtained using *Corynebacterium glutamicum* and *Yarrowia lipolytica* are shown in Table 17 below.

TABLE 17

| | Final product obtained from granulation of Corynebacterium glutamicum | Final product obtained from granulation of Yarrowia lipolytica |
|---|---|---|
| N-acetyl-L-mthionine content | 68% | 65% |
| Protein content | 15% | 19% |
| Crude fat content | — | 11% |
| Moisture content | 0.24% | 0.24% |
| Apparent density | 682.5 kg/m$^3$ | 682.5 kg/m$^3$ |
| Inorganic compound content | 1.88% | 1.88% |
| Particle size less than or equal to 500 μm | 2% | 4% |
| Particle size greater than 500 μm, but less than or euqal to 1000 μm | 28% | 29% |
| Particle size greater than 1000 μm, but less than or equal to 1300 μm | 66% | 63% |
| Particle size greater than 1300 μm | 4% | 4% |

Accordingly, the N-acetyl-L-methionine prepared in the present disclosure may exhibit high bypass rate as the amount of the N-acetyl-L-methionine degraded by microorganisms in the rumen is relatively small, in comparison with L-methionine. Additionally, the N-acetyl-L-methionine exhibits high digestive degradation rate, and the improvement effect of the milk fat and milk protein due to substantially feeding the N-acetyl-L-methionine to dairy cows was observed. These results suggest that the N-acetyl-L-methionine prepared based on the preparation methods of the present disclosure may be very usefully utilized as the feed additive for ruminants. Additionally, the environmentally friendly effect compared to petroleum-derived materials may be obtained by feeding the bio-based N-acetyl-L-methionine to ruminants.

From the foregoing, one of ordinary skill in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A method for producing bio-based N-acetyl-L-methionine, comprising:
    (a) producing L-methionine by microorganism fermentation; and
    (b) acetylating the L-methionine using a N-acetyltransferase or a microorganism producing the N-acetyltransferase, wherein the N-acetyltransferase is selected from the group consisting of *Pseudomonas putida*-derived N-acetyltransferase (ppmat), *Bacillus subtilis*-derived N-acetyltransferase (bsmat), and *Enterobacter* sp. 638-derived N-acetyltransferase (entmat).

2. The method according to claim 1, wherein producing the L-methionine by microorganism fermentation in (a) is carried out by:

(i) producing a precursor of L-methionine by microorganism fermentation; and (ii) producing L-methionine from the precursor of L-methionine by enzymatic conversion.

3. The method according to claim 2, wherein the precursor of L-methionine is O-acetyl-L-homoserine or O-succinyl-L-homoserine.

4. The method according to claim 2, wherein the enzymatic conversion is carried out by at least one enzyme selected from the group consisting of cystathionine-γ-synthase, O-acetyl homoserine sulfhydrylase, and O-succinyl homoserine sulfhydrylase.

5. The method according to claim 1, wherein producing L-methionine in step (a) is carried out by direct fermentation of L-methionine-producing strains.

6. The method according to claim 1, further comprising supplying acetyl-CoA in the step (b).

7. The method according to claim 1, wherein producing the L-methionine in step (a) and acetylating the L-methionine in step (b) is carried out by direct fermentation of the microorganism producing the N-acetyltransferase so that the microorganism directly produces N-acetyl-L-methionine.

8. The method according to claim 7, further comprising supplying bio-based L-methionine to a medium during the direct microorganism fermentation.

9. The method according to claim 1, wherein 50% to 100% of carbon constituting the bio-based N-acetyl-L-methionine is carbon derived from bioresources.

10. A method for producing a feed additive or feed composition, comprising:

(1) preparing the bio-based N-acetyl-L-methionine produced by the method of claim 1 or a salt thereof; and (2) mixing the bio-based N-acetyl-L-methionine of (1) with an animal feed.

11. The method according to claim 10, wherein the bio-based N-acetyl-L-methionine is in an amount of 0.01 wt % to 90 wt % relative to the total weight of the animal feed.

12. A method for feeding, comprising:

preparing a feed additive or feed composition containing bio-based N-acetyl-L-methionine or a salt thereof according to the method of claim 10; and feeding the feed additive or feed composition to a ruminant.

13. A method for increasing L-methionine absorption of the liver, the small intestine, or a combination thereof, the method comprising:

feeding a feed additive or feed composition according to the method of claim 12 to the ruminant, thereby bypassing the rumen.

14. The method of claim 13, wherein rumen bypass efficiency of the N-acetyl-L-methionine is higher than rumen bypass efficiency of L-methionine.

15. The method of claim 13, wherein N-acetyl-L-methionine is converted into L-methionine by a digestive enzyme in the small intestine or liver.

16. A method for improving milk production, milk fat, or milk protein, a weight-gain effect of a ruminant, or a combination thereof, the method comprising feeding a feed additive or feed composition according to the method of claim 12, thereby bypassing the rumen.

17. The method of claim 16, wherein rumen bypass efficiency of the N-acetyl-L-methionine is higher than rumen bypass efficiency of L-methionine.

18. The method of claim 16, wherein N-acetyl-L-methionine is converted into L-methionine by a digestive enzyme in the small intestine or liver.

* * * * *